(12) United States Patent
Lee et al.

(10) Patent No.: US 8,361,392 B2
(45) Date of Patent: Jan. 29, 2013

(54) BIOCHIP HAVING IMAGE SENSOR WITH BACK SIDE ILLUMINATION PHOTODIODE

(75) Inventors: Byoung Su Lee, Yeosu-si (KR); Do Young Lee, Seongnam-si (KR)

(73) Assignee: Siliconfile Technologies Inc., Seoul (KR)

( * ) Notice: Subject to any disclaimer, the term of this patent is extended or adjusted under 35 U.S.C. 154(b) by 198 days.

(21) Appl. No.: 12/985,083

(22) Filed: Jan. 5, 2011

(65) Prior Publication Data

US 2011/0172129 A1 Jul. 14, 2011

(30) Foreign Application Priority Data

Jan. 14, 2010 (KR) .................. 10-2010-0003420

(51) Int. Cl.
- *G01N 21/00* (2006.01)
- *C40B 60/00* (2006.01)
- *H01L 31/0232* (2006.01)
- *H01L 31/00* (2006.01)
- *G01N 21/64* (2006.01)
- *G01J 1/58* (2006.01)

(52) U.S. Cl. .............. 422/82.05; 422/82.06; 422/82.07; 422/82.08; 422/82.09; 422/82.11; 506/33; 506/39; 250/458.1; 435/287.2; 435/288.7; 257/432; 257/460

(58) Field of Classification Search .................. None
See application file for complete search history.

(56) References Cited

U.S. PATENT DOCUMENTS

2004/0234417 A1* 11/2004 Schienle et al. .......... 422/82.08

FOREIGN PATENT DOCUMENTS

| EP | 2 221 606 | 8/2010 |
|---|---|---|
| WO | 2007/148891 | 12/2007 |
| WO | 2008/140158 | 11/2008 |
| WO | 2009/011535 | 1/2009 |
| WO | 2009/066896 | 5/2009 |

* cited by examiner

*Primary Examiner* — Neil N Turk
(74) *Attorney, Agent, or Firm* — Kile Park Goekjian Reed & McManus PLLC

(57) ABSTRACT

A biochip having an image sensor with a back side illumination photodiode structure includes: a biochip layer; and an image sensor layer attached to one surface of the biochip layer and configured to sense light with biochemical reaction information, which is emitted from the biochip layer, wherein the image sensor layer includes a plurality of light sensing parts which receive the light directed toward a back side of a wafer.

7 Claims, 1 Drawing Sheet

BIOCHIP HAVING IMAGE SENSOR WITH BACK SIDE ILLUMINATION PHOTODIODE

BACKGROUND OF THE INVENTION

1. Field of the Invention

The present invention relates to a biochip, and more particularly, to a biochip having an image sensor with a back side illumination photodiode structure which collects light from the back side of a wafer in order to improve capability of sensing light emitted from reaction regions of a biochip.

2. Description of the Related Art

In general, a biochip is manufactured in a type in which reference samples constituted biological molecules such as DNAs, proteins and the likes are regularly arranged on a substrate made of a material such as glass, silicon and nylon.

Biochips are divided into a DNA chip, a protein chip, and so forth, depending upon the kind of reference samples to be arranged. Basically, a biochip uses biochemical reactions between reference samples and target samples which are fixed with respect to a substrate. Representative examples of the biochemical reactions between the reference samples and the target samples include a complementary binding of DNA bases and an antigen-antibody reaction.

For the most part, diagnosis by a biochip is implemented by detecting a degree to which a biochemical reaction occurs, through an optical procedure using an image sensor. The optical procedure generally uses a fluorescence or luminescence phenomenon.

FIG. 1 is a view illustrating the configuration of a conventional biochip having an image sensor with a front side illumination photodiode structure.

Referring to FIG. 1, a conventional biochip 100 having an image sensor with a front side illumination photodiode structure includes a biochip layer 100a and an image sensor layer 100b.

The biochip layer 100a has a plurality of first reaction region 110a, second reaction region 110b and third reaction region 110c which have shapes of grooves. The first, second and third reaction regions 110a, 110b and 110c respectively have target samples 111a, 111b and 111c in the upper portions thereof and reference samples 112a, 112b and 112c in the lower portions thereof.

The image sensor layer 110b has a plurality of first front side illumination photodiode 151a (PD1), second front side illumination photodiode 151b (PD2) and third front side illumination photodiode 151c (PD3) which are formed in an epitaxial layer 150 of a wafer.

A plurality of stacked metal wiring lines 131 and 133 are formed in an interlayer dielectric 130 which is formed on the upper surface of the epitaxial layer 150.

However, in the conventional biochip 100 having an image sensor with a front side illumination photodiode structure, light 120, which is emitted depending upon degrees of biochemical reactions between the target samples 111a, 111b and 111c and the reference samples 112a, 112b and 112c of the plurality of first, second and third reaction regions 110a, 110b and 110c, is likely to be absorbed by the metal wiring lines 131 and 132 which are formed over the plurality of first, second and third front side illumination photodiodes 151a, 151b and 151c, as a result of which the light sensitivity of the plurality of first, second and third front side illumination photodiodes 151a, 151b and 151c may be degraded.

Meanwhile, in the manufacture of the biochip layer, a surface treatment technology is regarded important for the attachment of bio-materials. That is to say, in order to allow the bio-materials to be easily attached to a substrate, surface treatment is performed in such a way as to provide hydrophilicity or hydrophobicity. Such surface treatment is performed mainly using plasma.

In the conventional structure adopting the front side illumination (FSI), as the plasma is incident on the photodiodes during the surface treatment, the dark current of the photodiodes may be increased. Further, due to the fact that the biochip layer is formed on the interlayer dielectric, solutions, which are employed in the manufacture and reaction procedures of the biochip layer, may infiltrate into underlying circuits by passing through the interlayer dielectric. As a consequence, problems may be caused in that it is difficult to form the interlayer dielectric and limitations may exist in performing the surface treatment for the biochip layer and using reacting solutions, etc.

SUMMARY OF THE INVENTION

Accordingly, the present invention has been made in an effort to solve the problems occurring in the related art, and an object of the present invention is to provide a biochip having an image sensor with a back side illumination photodiode structure which can directly collect light with biochemical reaction information, emitted from a biochip layer, so as to improve light sensitivity, and can prevent the characteristics of circuits from deteriorating due to surface treatment conducted during a manufacturing procedure of the biochip layer and infiltration of a solution occurring during a biochemical reaction procedure.

In order to achieve the above object, according to one aspect of the present invention, there is provided a biochip having an image sensor with a back side illumination photodiode structure, including: a biochip layer; and an image sensor layer attached to one surface of the biochip layer and configured to sense light with biochemical reaction information, which is emitted from the biochip layer, wherein the image sensor layer includes a plurality of light sensing parts which receive the light directed toward a back side of a wafer.

BRIEF DESCRIPTION OF THE DRAWINGS

The above objects, and other features and advantages of the present invention will become more apparent after a reading of the following detailed description taken in conjunction with the drawings, in which.

DETAILED DESCRIPTION OF PREFERRED EMBODIMENTS

Figure 1:
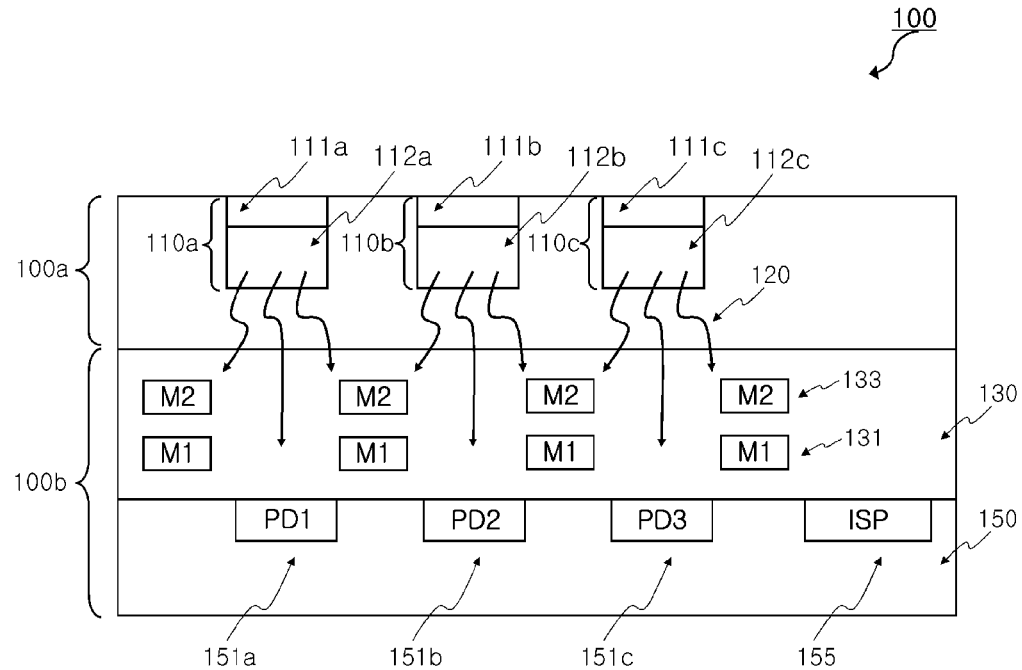
FIG. 1 is a view illustrating the configuration of a conventional biochip having an image sensor with a front side illumination photodiode structure.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 2:
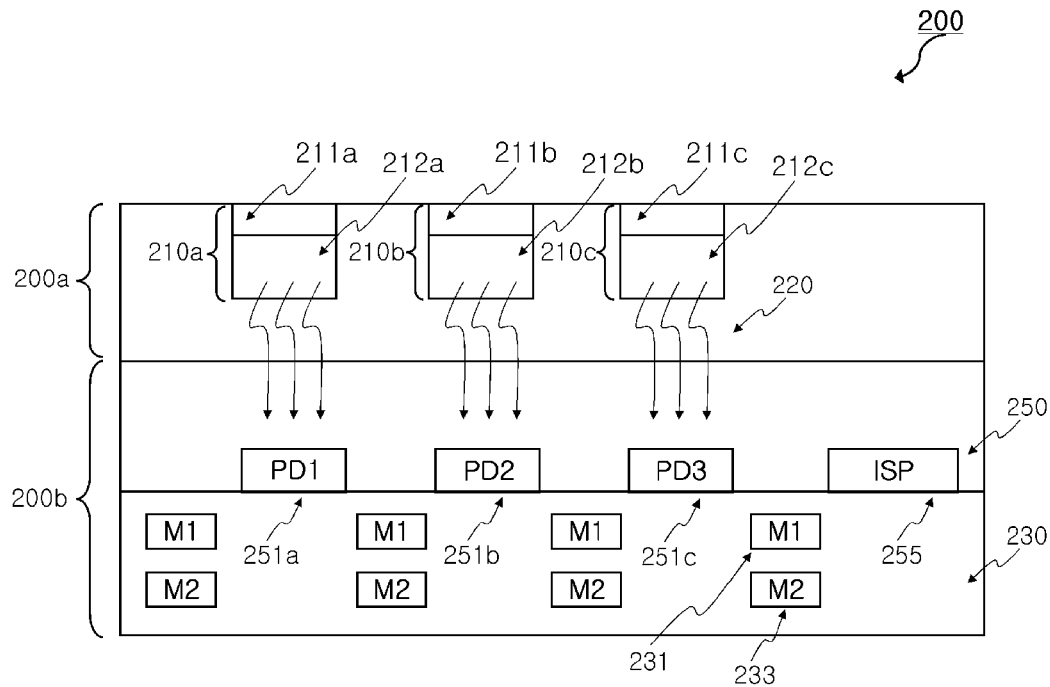
FIG. 2 is a view illustrating the configuration of a biochip having an image sensor with a back side illumination photodiode structure in accordance with an embodiment of the present invention.

FIG. 2 is a view illustrating the configuration of a biochip having an image sensor with a back side illumination photodiode structure in accordance with an embodiment of the present invention.

Referring to FIG. 2, a biochip 200 having an image sensor with a back side illumination photodiode structure in accordance with an embodiment of the present invention includes a biochip layer 200a and an image sensor layer 200b.

The biochip layer 200a has a plurality of first reaction region 210a, second reaction region 210b and third reaction region 210c which have shapes of grooves.

The first reaction region 210a has a target sample 211a in the upper portion thereof and a reference sample 212a in the lower portion thereof. Similarly, the second reaction region 210b has a target sample 211b in the upper portion thereof and a reference sample 212b in the lower portion thereof, and the third reaction region 210c has a target sample 211c in the upper portion thereof and a reference sample 212c in the lower portion thereof.

Hereafter, functions of the target sample 211a and the reference sample 212a of the first reaction region 210a will be mainly described in detail.

The target sample 211a may be used to include a luminescent material which emits light by itself when external illumination is blocked. A representative example of the luminescent material is luciferin. Luciferin becomes active luciferin when activated by ATP (adenosine tri-phosphate). As the active luciferin is oxidated under the action of luciferase and becomes oxyluciferin, chemical energy is converted into light energy and light is produced.

Also, the target sample 211a may be used to include a fluorescent material which can generate light of a specified wavelength band by external illumination (not shown). The fluorescent material may be produced in the first reaction region 210a as a result of a reaction between the reference sample 212a and the target sample 211a, or may be produced in such a manner that an optional fluorescent material such as GFP (green fluorescence protein) is left in the first reaction region 210a after a specified biochemical reaction is induced between the reference sample 212a and the target sample 211a by binding the optional fluorescent material with the target sample 211a.

The reference sample 212a may include different materials depending upon which biochemical reaction is targeted. For example, if the biochemical reaction is an antigen-antibody reaction, the reference sample 212a may be an antigen, and if the biochemical reaction is a complementary binding of DNA bases, the reference sample 212a may be a gene which is genetically engineered to be capable of complementary binding.

The target sample 211a is selected depending upon the reference sample 212a which is determined according to the kind of the biochemical reaction. For example, if the reference sample 212a is an antigen, the target sample 211a may be blood, and the like, and if the reference sample 212a is a genetically engineered gene, the target sample 211a may be a user's gene, and the like.

The image sensor layer 200b has a configuration which is placed on the bottom surface of the biochip layer 200a and forms a back side illumination (BSI) image sensor.

The back side illumination (BSI) image sensor is formed by performing the same processes as the conventional front side illumination (FSI) image sensor and by finally overturning a processed wafer such that the resultantly obtained image sensor can directly collect light.

That is to say, when observed from the standpoint of the conventional front side illumination (FSI) image sensor, the back side illumination (BSI) image sensor according to the present invention collects light from the bottom portions of the photodiodes, that is, the bottom surface of the wafer.

The image sensor layer 200b has a plurality of first back side illumination photodiode 251a (PD1), second back side illumination photodiode 251b (PD2), and third back side illumination photodiode 251c (PD3) which are formed in an epitaxial layer 250 of the wafer.

The first back side illumination photodiode 251a (PD1) senses light 220 which is emitted from the first reaction region 210a depending upon a degree of a biochemical reaction between the target sample 211a and the reference sample 212a in the first reaction region 210a. Similarly, the second back side illumination photodiode 251b (PD2) senses light 220 which is emitted from the second reaction region 210b depending upon a degree of a biochemical reaction between the target sample 211b and the reference sample 212b in the second reaction region 210b, and the third back side illumination photodiode 251c (PD3) senses light 220 which is emitted from the third reaction region 210c depending upon a degree of a biochemical reaction between the target sample 211c and the reference sample 212c in the third reaction region 210c.

The light 220, which is respectively emitted from the first reaction region 210a, the second reaction region 210b and the third reaction region 210c, directly reaches and is absorbed by the first back side illumination photodiode 251a (PD1), the second back side illumination photodiode 251b (PD2) and the third back side illumination photodiode 251c (PD3), without passing by metal wiring lines which are stacked over the photodiodes in the formation of the conventional front side illumination (FSI) image sensor, whereby light sensitivity can be significantly improved according to the present invention.

The light sensed by the first back side illumination photodiode 251a (PD1), the second back side illumination photodiode 251b (PD2) and the third back side illumination photodiode 251c (PD3) is outputted as electrical signals. The electrical signals are processed by a signal processing unit such as an ISP (image signal processor) 255 which is provided in the image sensor layer 200b.

Preferably, the upper portion of the epitaxial layer 250 may include optical filters (not shown) which transmit light of a preselected band and micro lenses (not shown) which focus light on the optical filters.

An interlayer dielectric 230 is disposed under the epitaxial layer 250 and a plurality of stacked metal wiring lines 231 and 233 are formed in the interlayer dielectric 230. This structure is distinguished from the structure of the conventional front side illumination (FSI) image sensor in which the interlayer dielectric 130 is disposed on the epitaxial layer 150 and the metal wiring lines 131 and 133 are formed in the interlayer dielectric 130.

In the conventional structure using front side illumination (FSI), due to the fact that the biochip layer is formed on the interlayer dielectric, the characteristics of the photodiodes are likely to be changed due to surface treatment implemented during a procedure of manufacturing the biochip layer, and reacting solutions may influence underlying circuits by passing through the interlayer dielectric.

However, in the present structure using back side illumination (BSI), since the biochip layer is formed on a back side which faces away from a region where circuits are formed, the characteristics of the photodiodes are not influenced by the surface treatment implemented during a procedure of manufacturing the biochip layer, and it is possible to prevent misoperation of circuits from being caused due to infiltration of solutions used in reaction procedures.

As is apparent from the above description, in the embodiment of the present invention, due to the fact that light with biochemical reaction information, which is emitted from a biochip layer, is directly collected at the bottom portion of a back side illumination photodiode structure, that is, at the bottom surface of a wafer, light sensitivity can be improved.

Also, in the embodiment of the present invention, it is possible to prevent the characteristics of circuits from deteriorating due to surface treatment conducted during a manufacturing procedure of the biochip layer and infiltration of a solution occurring during a biochemical reaction procedure.

Although a preferred embodiment of the present invention has been described for illustrative purposes, those skilled in the art will appreciate that various modifications, additions and substitutions are possible, without departing from the scope and the spirit of the invention as disclosed in the accompanying claims.

What is claimed is:

1. A biochip having an image sensor with a back side illumination photodiode structure, comprising:
   a biochip layer; and
   an image sensor layer attached to and disposed below the biochip layer and configured to sense light with biochemical reaction information, which is emitted from the biochip layer,
   wherein the image sensor layer includes a plurality of light sensing parts which receive the light directed toward a back side of a wafer, and wherein the light sensing parts comprise a plurality of back side illumination photodiodes which are formed in an epitaxial layer of the wafer; and
   wherein an interlayer dielectric is formed under the epitaxial layer, and a plurality of metal wiring lines are formed in the interlayer dielectric.

2. The biochip according to claim 1,
   wherein the biochip layer includes a plurality of reaction regions which have shapes of grooves, and
   wherein each of the reaction regions has a target sample in an upper portion thereof and a reference sample in a lower portion thereof.

3. The biochip according to claim 2, wherein the target sample includes a luminescent material or a fluorescent material.

4. The biochip according to claim 2, wherein the reference sample uses an antigen material when a biochemical reaction is an antigen-antibody reaction, and uses a gene which is genetically engineered to be capable of complementary binding, when a biochemical reaction is a complementary binding of DNA bases.

5. The biochip according to claim 1, wherein light sensed by the back side illumination photodiodes is outputted as electrical signals, and the electrical signals are processed by a signal processing unit.

6. The biochip according to claim 5, wherein the signal processing unit comprises an ISP (image signal processor) which is provided in the image sensor layer.

7. The biochip according to claim 1, wherein an upper portion of the epitaxial layer includes optical filters and micro lenses which are formed over the optical filters.

* * * * *